(12) United States Patent
Murphy et al.

(10) Patent No.: US 8,501,197 B2
(45) Date of Patent: Aug. 6, 2013

(54) **COMPOSITIONS AND METHODS FOR STIMULATING IMMUNE RESPONSE AGAINST *MORAXELLA CATARRHALIS***

(75) Inventors: Timothy F. Murphy, East Amherst, NY (US); Min Yang, Amherst, NY (US)

(73) Assignee: The Research Foundation for The State of New York, Amherst, NY (US)

( * ) Notice: Subject to any disclaimer, the term of this patent is extended or adjusted under 35 U.S.C. 154(b) by 0 days.

(21) Appl. No.: 13/695,093

(22) PCT Filed: Apr. 29, 2011

(86) PCT No.: PCT/US2011/034541
§ 371 (c)(1),
(2), (4) Date: Jan. 25, 2013

(87) PCT Pub. No.: WO2011/137334
PCT Pub. Date: Nov. 3, 2011

(65) Prior Publication Data
US 2013/0129765 A1    May 23, 2013

Related U.S. Application Data

(60) Provisional application No. 61/329,825, filed on Apr. 30, 2010.

(51) Int. Cl.
*A61K 39/102* (2006.01)
*A61K 39/02* (2006.01)
*A61K 39/385* (2006.01)
*A61K 39/00* (2006.01)
*A61K 38/00* (2006.01)
*C07K 1/00* (2006.01)

(52) U.S. Cl.
USPC ............. 424/255.1; 424/190.1; 424/193.1; 424/184.1; 424/234.1; 514/1.1; 530/350; 530/825

(58) Field of Classification Search
None
See application file for complete search history.

(56) References Cited

U.S. PATENT DOCUMENTS

| | | |
|---|---|---|
| 6,673,910 B1 * | 1/2004 | Breton .................. 536/23.1 |
| 2007/0010665 A1 | 1/2007 | Breton |
| 2007/0087019 A1 | 4/2007 | Tucker et al. |
| 2009/0169577 A1 | 7/2009 | Murphy et al. |

OTHER PUBLICATIONS

M. Tanabe et al., The ABC Transporter Protein OppA Provides Protection against Experimental *Yersinia pestis* Infection, Infect. Immun., Jun. 2006, vol. 74, No. 6, pp. 3687-3691.

M. Yang et al., Characterization and Evaluation of the *Moraxella catarrhalis* Oligopeptide Permease A (OppA) as a Mucosal Vaccine Antigen, Infect. Immun., Epub Dec. 6, 2010, vol. 79, No. 2, pp. 846-857.

* cited by examiner

*Primary Examiner* — S. Devi
(74) *Attorney, Agent, or Firm* — Hodgson Russ LLP

(57) ABSTRACT

This invention provides a method for stimulating in an individual an immune response against *M. catarrhalis*. The method comprises administering to an individual a composition comprising *M. catarrhalis* OppA protein in an amount effective to stimulate an immune response against *M. catarrhalis* in the individual.

14 Claims, 7 Drawing Sheets

COMPOSITIONS AND METHODS FOR STIMULATING IMMUNE RESPONSE AGAINST *MORAXELLA CATARRHALIS*

CROSS REFERENCE TO RELATED APPLICATIONS

This application claims the priority of U.S. Provisional application No. 61/329,825, filed on Apr. 30, 2010, the disclosure of which is incorporated herein by reference.

STATEMENT REGARDING FEDERALLY SPONSORED RESEARCH OR DEVELOPMENT

This invention was made with government support under Grant No. R01 AI 28304 from the National Institutes of Health. The Government has certain rights in the invention.

FIELD OF THE INVENTION

This invention relates to field of *Moraxella catarrhalis* infections and more particularly to an immunogenic composition against *Moraxella catarrhalis*.

BACKGROUND OF THE INVENTION

*Moraxella catarrhalis* is a common cause of otitis media in children and of lower respiratory tract infections in adults with chronic obstructive pulmonary disease; therefore, these two groups would benefit from a vaccine to prevent *M. catarrhalis* infections. *Moraxella catarrhalis* is a Gram-negative *diplococcus* frequently found as a commensal of the upper respiratory tract. However, over the past 2 to 3 decades this bacterium has emerged from being considered as a harmless commensal to being recognized as a genuine respiratory tract pathogen of serious public health concerns.

Acute otitis media is the most common bacterial infection in children with 70% experiencing at least one episode by age 3. *M. catarrhalis* is the third leading cause of otitis media after *Streptococcus pneumoniae* and nontypeable *Haemophilus influenzae*. *M. catarrhalis* is associated with 25% of acute otitis media by culture and 46.4% of chronic middle ear effusion by PCR. In addition, the nasopharyngeal carriage rate of *M. catarrhalis* in children is high (up to 75%) and the frequency of colonization is positively related to the development of otitis media.

In adults, *M. catarrhalis* is the second most common bacterial cause of exacerbations of chronic obstructive pulmonary disease (COPD) after non-typeable *H. influenzae*. COPD is the fourth leading cause of death in the United States, affecting 24 million Americans. *M. catarrhalis* causes approximately 10% of exacerbations of COPD, accounting for 2 to 4 million episodes annually. Furthermore, *M. catarrhalis* also colonizes the lower respiratory tract in up to 2.5 to 10% of adults with COPD at their stable states. Lower airway colonization contributes to airway inflammation in COPD as a result of sloughing of highly inflammatory bacterial cell wall antigens into the airway.

*M. catarrhalis* is a nonencapsulated bacterium and does not secrete exotoxin. The current vaccine studies have mostly focused on various outer membrane proteins (OMPs) as vaccine candidates. To date, a limited number of OMPs have been examined and are currently under different stages of evaluation as part of an effort to develop a multicomponent vaccine against *M. catarrhalis*.

SUMMARY OF THE INVENTION

The present invention provides a novel protein, Oligopeptide permease protein A (OppAs), as an antigen for use in a vaccine against *M. catarrhalis*. The protein is characterized in terms of sequence conservation and immunogenicity. This protein is predicted to have a periplasmic location and therefore its ability to induce an immune response and/or protection against *Moraxella catarrhalis* infection was surprising. However, three independent sets of experiments described below demonstrated that OppA also expresses epitopes on the bacterial surface, a novel and surprising observation. It is believed that induction of potentially protective immune responses is due to immune responses to OppAs epitopes on the bacterial surface.

In one aspect, the present invention provides a method for stimulating in an individual an immune response against *M. catarrhalis*. The method comprises administering to an individual a composition comprising *M. catarrhalis* OppA protein. The immune response stimulated in the individual may be a prophylactic or a therapeutic immune response. The stimulated immune response may comprise stimulation of an *M. catarrhalis* specific humoral immune response, such as by generation of antibodies in the individual against *M. catarrhalis* and/or *M. catarrhalis* specific cell-mediated immune response. In one embodiment of the invention, performing the method of the invention results in an enhanced rate of *M. catarrhalis* bacterial clearance from the lungs of an individual to whom the composition is administered.

In one aspect, the present invention provides immunogenic compositions which will elicit an immune response against *M. catarrhalis*. The compositions comprise *M. catarrhalis* OppA protein and optionally, an adjuvant suitable for the route of administration. For example, if the immunogenic composition is to be administered intranasally, then an adjuvant suitable for mucosal administration can be used.

DETAILED DESCRIPTION OF THE INVENTION

Figure 1:
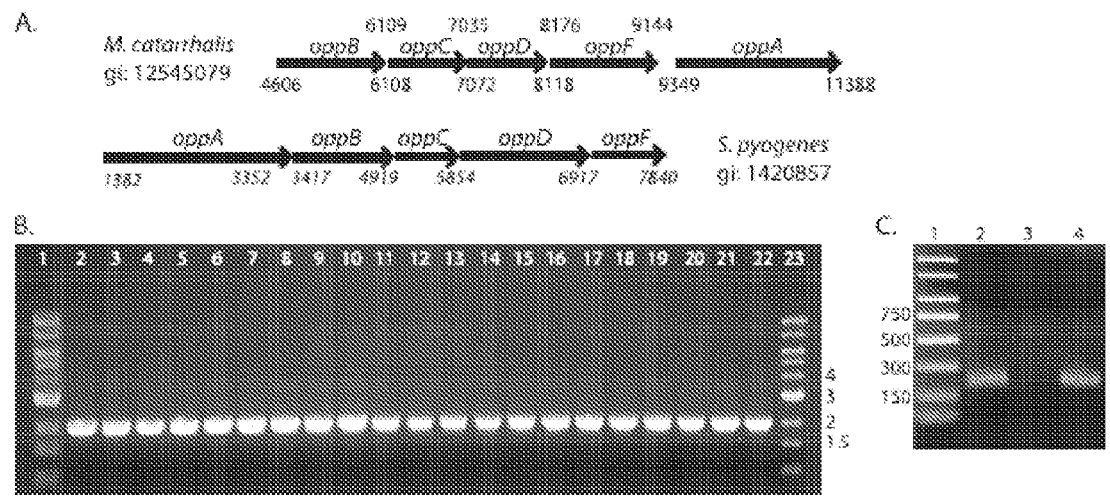
FIG. 1. Characterization of the oppA gene. (A) Schematic illustration of oppA with the other oligopeptide transporter genes in the genome of *M. catarrhalis* ATCC 43617 and *S. pyogenes*. Numbers indicate the initial and terminal nucleotide positions of each gene within the GenBank sequence. (B) Ethidium bromide stained agarose gel showing amplicons of oppA gene amplified from 20 clinical isolates of *M. catarrhalis* and the ATCC 43617 strain. Lane 1 and 23: DNA standards, lane 2 to 11: amplicons from middle ear fluid isolates: 135, 238, 555, 2901, 3584, 3614, 5488, 6952, 8184, and 9483, respectively; lane 12: amplicon from ATCC 43617; lane 13 to 22: amplicons from sputum isolates: 5P34B1, 10P58B2, 12P15B1, 14P25B1, 29P24B1, 33P25B2, 39P29B2, 55P18B3, 63P62B1, and 96P9B1, respectively. The sizes of the DNA standards (in kilobases) are indicated on the right. (C) Results of reverse transcriptase (RT) PCR with RNA extracted from *M. catarrhalis* O35E to detect oppA transcript. Lane 1, DNA standards; lane 2, RT-PCR product; lane 3, RT-PCR reaction in the absence of reverse transcriptase; lane 4: PCR product from genomic DNA template. DNA standards are noted in base pairs on the left.

The present invention provides a method for stimulating in an individual an immune response against *M. catarrhalis*. The method comprises administering to the individual a composition comprising *M. catarrhalis* OppA protein. The OppA protein is provided in an amount effective to stimulate an immune response against *M. catarrhalis* in the individual.

The present invention also provides immunogenic compositions comprising *M. catarrhalis* OppA protein, which when administered to an individual provides immunity against *M. catarrhalis* infection. Thus, the OppA protein in the composition comprises one or more immunogenic antigens that can stimulate an *M. catarrhalis* specific humoral and/or a cell mediated immune response in the individual. The amino acid sequence of OppaA protein is provided in SEQ ID NO:1. A representative cDNA sequence encoding this OppA protein is provided in SEQ ID NO:2. The immunogenic compositions may comprise one or more adjuvants or other pharmaceutical carriers.

We discovered the oppA gene in our search for surface proteins of *M. catarrhalis*. Homology analysis suggested that oppA encodes a soluble periplasmic protein of the oligopeptide transport system. Given its periplasmic localization, OppA did not stand out as a candidate for a potential vaccine and therefore, the observation that OppA of *M. catarrhalis* expresses epitopes on the bacterial surface was surprising. While not intending to be bound by any particular theory, one possibility is that OppA epitopes are intermittently exposed when they bind oligopeptides from the environment for transport across the periplasm. Alternatively, the protein may be intermittently exposed during bacterial cell wall turnover and cell division, or the protein has more than one location in the bacterial cell wall.

We found that OppA is highly conserved among strains of *M. catarrhalis*. Sequence conservation can be a result of selection pressure to preserve the essential physiological function of the protein. Sequence conservation of oppA gene would also be consistent with its presumed periplasmic localization. Genes that encode surface exposed proteins in *H. influenzae* undergo point mutations driven by immune selective pressure during colonization; these changes allow the bacterium to evade host immune responses. Therefore, again, it was surprising that OppA, which is highly conserved and predominantly present in the periplamic region, could impart immune protection to an individual against the bacterium. While not intending to be bound by any particular theory, we believe OppA is presumably not continuously displayed to the host immune system.

In this work, we evaluated the potential of *M. catarrhalis* OppA protein as a vaccine antigen. We showed that OppA 1) is highly conserved among strains of *M. catarrhalis* that cause otitis media and exacerbations of COPD; 2) is an efficient immunogen, 3) expresses epitopes that are exposed on the bacterial surface; and 4) induces potentially protective immune responses following mucosal immunization in the mouse pulmonary clearance model.

Currently the mouse pulmonary clearance model is the most widely used model to assess potential vaccine antigens of *M. catarrhalis*. The model is simple, reproducible, is performed in multiple centers and measures a functional response. The observation that intranasal immunization of OppA induced enhanced pulmonary clearance provides support for a mucosal route of immunization for *M. catarrhalis* infections which are predominantly mucosal infections.

Isolated protein used in the method of the invention may be obtained by methods known to those skilled in the art, such as by isolation of the proteins from *M. catarrhalis* cultures, or by producing the proteins recombinantly from expression vectors inserted into cells using conventional techniques, culturing the cells under conditions whereby the proteins are synthesized by the cells, and isolating the proteins from the cells according to established procedures.

The isolated *M. catarrhalis* OppA may be purified to any desired degree of purification. Methods for protein purification are well known in the art and are applicable to preparing purified *M. catarrhalis* OppA protein for use in the present invention. In various embodiments, the *M. catarrhalis* OppA protein used in the invention may be partially purified, substantially purified, or fully purified. In various embodiments, the compositions of the present invention may comprise *M. catarrhalis* OppA protein, may consist essentially of *M. catarrhalis* OppA protein, or may consist of *M. catarrhalis* OppA protein. In some embodiments, the OppA protein may be used with one or more of additional *M. catarrhalis* immunogenic proteins (such as outer membrane proteins) for an antigenic formulation. In additional embodiments, the invention provides fragments of the OppA protein for use in stimulating a specific immune response against *M. catarrhalis* in an individual. Given the benefit of the present disclosure, those skilled in the art will be able to recognize suitable fragments of the OppA protein so that peptides for eliciting a specific immune response against *M. catarrhalis* in an individual can be produced. In general, suitable peptides comprise or consist of at least 9 contiguous amino acids of SEQ ID NO:1 Thus, the invention includes all peptides that comprise or consist of each 9 amino acid segment of SEQ ID NO:X across its entire length, and which can vary in length from 9 amino acids, up to one amino acid less than the full length of SEQ ID NO:X. In one embodiment, the length is from 9 to 20 amino acids, inclusive.

Homology Modeling of *M. catarrhalis* OppA.

Peptides of the invention can be designed based on protein homology modeling. A model of *M. catarrhalis* OppA was generated using the crystal structure of *S. clavuligerus* OppA2 (an arginine peptide binding molecule as is *M. catarrhalis* OppA) bound with arginine (Mackenzie A K, Valegard K, Iqbal A, Caines M E, Kershaw N J, Jensen S E, Schofield C J, Andersson I. Crystal structures of an oligopeptide-binding protein from the biosynthetic pathway of the beta-lactamase inhibitor clavulanic acid. J Mol. Biol. 2010; 396(2):332-44) (PDB ID 2WOP) as the template. Initially, the Fold and Function Assignment web server (Jaroszewski L, Rychlewski L, Li Z, Li W, Godzik A. FFAS03: a server for profile-profile sequence alignments. Nucleic Acids Res. 2005; 33 (Web Server issue):W284-8. PMCID: 1160179) was utilized to identify structural homologs based on sequence alignment. We chose *S. clavuligerus* OppA2 as a template given that a high-resolution crystal structure had been determined with arginine bound in the active site cleft. ProtMod, part of the FFAS server, was then used to build the all-atom homology model. The model has ~80% coverage (538 of 679 residues) of the *M. catarrhalis* OppA sequence. Of the 141 residues unable to be modeled, 58 are in C-terminus of the protein, which is substantially longer than other members of the OppA family. The overall secondary structure predicted for the *M. catarrhalis* OppA is highly conserved and consistent with that observed for other OppA proteins whose crystal structures have been determined. Structural analyses confirmed that three domains form two lobes, with the peptide-binding site located in the cleft between the two lobes (Quiocho F A, Ledvina P S. Atomic structure and specificity of bacterial periplasmic receptors for active transport and chemotaxis: variation of common themes. Mol. Microbiol. 1996; 20(1):17-25) Our homology model is consistent with these structures. This homology model can be to design peptides for use in the invention, and in particular embodiment, the peptides are fragments of disordered regions that contain *M. catarrhalis*-specific sequences, which are predicted to be surface epitopes and thus are expected to contain peptide sequences that are suitable for use in making and using peptides according to the invention.

Compositions comprising the proteins, such as pharmaceutical compositions for administration to individuals, may be prepared by mixing the proteins with any suitable pharmaceutically acceptable carriers, excipients and/or stabilizers to obtain pharmaceutical compositions. Some examples of acceptable carriers, excipients and stabilizers suitable for combining with the proteins can be found in: *Remington: The Science and Practice of Pharmacy* (2005) 21st Edition, Philadelphia, Pa. Lippincott Williams & Wilkins.

The compositions of the invention may be administered in combination with any suitable adjuvant or adjuvant combination. In one embodiment, the mucosal adjuvant may be cholera toxin. Examples of other mucosal adjuvants include ISCOMs (immune stimulating complexes), CpG oligonucleotides, *E. coli* labile toxins, interleukins (including IL1α, IL5, IL6, IL12, IL15 and 18) and chemokines such as MCP1. In another embodiment, the adjuvant may be Freund's incomplete adjuvant. Examples of other adjuvants for systemic immunization include alum (aluminum salts), CpG oligonucleotides, organic compounds such as squalene, QS21, monophosphorylated lipid A and liposomes.

It is expected that the compositions used in the method of the invention may be administered to any mammal to stimulate an immune response against *M. catarrhalis* bacteria. In one embodiment, the mammal is a human.

The method can be performed by administering the composition to the individual via any acceptable method of delivery which enables the composition to stimulate an immune response to *M. catarrhalis* bacteria in the individual. Examples of acceptable administration routes include but are not limited to subcutaneous, intramuscular, intravenous, intradermal, intranasal, oral and inhalation administrations. In one embodiment, the compositions are administered subcutaneously. In another embodiment, the compositions are administered intransally.

It will be recognized by those of skill in the art that the form and character of the particular dosing regimen employed in the method of the invention will be dictated by the route of administration and other well-known variables, such as the size of the individual and the stage of the infection. It is generally considered that the amount of protein administered will range from approximately 10 micrograms to milligrams. Accordingly, in view of the present invention, one skilled in the art can determine an amount of isolated *M. catarrhalis* protein that is effective to stimulate an immune response against *M. catarrhalis* for any particular individual in need of such a stimulated immune response.

The immune response stimulated in the individual by the method of the invention may be a prophylactic or a therapeutic immune response. The stimulated immune response may comprise an *M. catarrhalis* specific humoral immune response, an *M. catarrhalis* specific cell-mediated response, or both. The humoral response may be a systemic response, a mucosal response, or both.

In one embodiment, the stimulated immune response comprises generation of antibodies in the individual that are specific to *M. catarrhalis* bacteria via specific binding of the antibodies to the protein to the bacteria. In one embodiment, the stimulated immune response comprises generation of antibodies that are specific to more than one strain of *M. catarrhalis* bacteria. The antibodies generated via stimulation of an immune response in the individual may by present in a variety of bodily fluids/tissues. Non-limiting examples of fluids in which the stimulated antibodies may be present include serum, sputum, saliva, nasopharyngeal secretions and middle ear fluid.

Stimulation of an immune response in an individual can be determined according to well known techniques. In one embodiment, stimulation of an immune response can be determined by detecting an increase in antibodies that recognize *M. catarrhalis* bacteria in an individual to whom a composition of the invention has been administered. An increase in antibodies in the individual that recognize *M. catarrhalis* bacteria can be detected using a variety of well known techniques, non-limiting examples of which include ELISAs and bactericidal assays. In one embodiment, an increase in antibodies to *M. catarrhalis* bacteria can be measured by determining an increase in antibodies to the isolated *M. catarrhalis* protein used in the composition administered to the individual.

The antibodies generated in the individual may comprise any antibody isotype. In various embodiments, the antibodies may be IgG antibodies, IgA antibodies, or combinations thereof.

In another embodiment, stimulation of an immune response to *M. catarrhalis* bacteria in an individual can be determined by detecting an enhanced rate of *M. catarrhalis* bacterial clearance from the lungs of an individual to whom the composition is administered, relative to the rate of *M. catarrhalis* bacterial clearance from the lungs of an individual to whom the composition has not been administered. In one embodiment, the immune response eradicates nasopharyngeal and/or or upper airway colonization by *M. catarrhalis*

The compositions of the invention may be administered in a single dose or in more than one dose. For example, in one embodiment, the composition may be administered as several doses over a period of time, such as by providing an initial administration, and subsequent administrations intended to boost the stimulation in immune response. The compositions of the invention may also be administered prior to, concurrently, or subsequent to conventional anti-bacterial treatments, such as antibiotic treatments.

The following Examples are meant to illustrate, but not limit the invention

EXAMPLE 1

Materials and Methods

Bacterial Strains and Growth.

*Moraxella catarrhalis* strain ATCC 43617 was obtained from the American Type Culture Collection (Manassas, Va.). Isolate 035E was provided by Eric Hansen. Strains 5P34B1, 10P58B2, 12P15B1, 14P25B1, 29P24B1, 33P25B2, 39P29B2, 55P18B3, 63P62B1, and 96P9B1 were sputum isolates obtained from adults with COPD. Strains 135, 238, 555, 2901, 3614, 3584, 5488, 8184, 9483, 6952 were middle ear fluid isolates obtained via tympanocentesis. Pulsed field gel electrophoresis of genomic DNA cut with SmaI showed that the strains are genetically diverse. *M. catarrhalis* strains were grown on brain heart infusion (BHI) plates at 37° C. with 5% $CO_2$ or in BHI broth with shaking at 37° C. Chemically competent *E. coli* strains Top10 and BL21(DE3) were obtained from Invitrogen (Carlsbad, Calif.) and were grown at 37° C. on Luria Bertani (LB) plates or in LB broth.

Nucleotide Sequence Analysis.

*M. catarrhalis* genes encoding putative surface proteins including lipoproteins and outer membrane proteins with characteristic signal sequences were identified based on the genome sequence of strain ATCC 43617 using a genome mining approach. oppA gene was defined by homolog analysis using a BLAST search at the NCBI website (://blast-.ncbi.nlm.nih.gov/Blast.cgi). The sequence of oppA genes amplified from 10 clinical isolates of *M. catarrhalis* and the ATCC 43617 strain were determined at the Roswell Park Cancer Institute DNA sequencing facility with sequencing primers P1, P5, and P6 listed in Table 1. These sequences were assembled with the Sequencher program and aligned with the ClustalW alignment function of the MacVector program.

Genomic DNA and RNA Purification.

Genomic DNA of *M. catarrhalis* strains was purified with the Wizard genomic DNA purification kit (Promega, Madison, Wis.) following the manufacturer's instructions. The total RNA of *M. catarrhalis* 035E was isolated with the Qiagen RNeasy mini kit (Qiagen, Valencia, Calif.) followed with DNase I treatment by using the RQ1 RNase-free DNase I from Promega and finally cleaned up with the Qiagen RNeasy mini kit following the protocols provided with the kits.

Reverse Transcriptase PCR(RT-PCR).

RT-PCR was performed using the Superscript II reverse transcriptase from Invitrogen (Carlsbad, Calif.). The first-strand cDNA was synthesized with 2 pmole of the reverse primer P3 (Table 1) and 1.5 μg of total RNA extracted from *M. catarrhalis* 035E strain. 10% cDNA reaction was then used in the second step PCR with both forward (P2) and reverse primers (P3) (Table 1) and Hotmaster mix (5 Prime Inc, Gaithersburg, Md.) to amplify a 223 bp fragment of the oppA gene. Parallel reaction without reverse transcriptase was performed as negative control to exclude amplification from contaminating DNA. 100 ng of genomic DNA extracted from *M. catarrhalis* 035E strain was used in PCR as positive control.

Overlap Extension PCR.

Overlap extension PCR is a PCR based strategy to create chimeric genes by fusion of independent fragments in the absence of restriction sites. We utilized overlap extension PCR to generate the linear double stranded DNA for oppA mutant construction via homologous recombination. The transforming DNA for an oppA mutant was composed of three fragments: F1/oppAUSG (oppA upstream gene sequence), F2/aphA-3 gene (kanamycin resistance gene), and F3/oppADSG (oppA downstream gene sequence). The location of these three fragments in relation to the oppA gene is depicted in FIG. 1A. Primers (P9 through P14) (Table 1) for each fragment were designed to include a 10 nt (nucleotides) 5' extension with sequence complementary to the end of the adjacent fragment. The resulting F1, F2 and F3 fragments would have 20 nt complementary overlapping region at adjacent ends, which are necessary for the fusion. The first step PCR was to amplify the three fragments individually with a high fidelity DNA polymerase pfu (Stratagene, Cedar Creek, Tex.). Genomic DNA extracted from *M. catarrhalis* strain 035E was used as template for F1 and F3 PCR. Plasmid pUC18K containing the nonpolar kanamycin resistance cassette was used as template for F2 PCR. F1, F2, and F3 were then purified by the Qiaquick PCR purification kit (Qiagen, Valencia, Calif.). Ten nmol of each purified fragment were mixed in the absence of additional primers in a second step PCR with pfu. The PCR program consisted of 10 repetitive cycles with a denaturing step at 94° C. for 30 s, an annealing step at 50° C. for 1 min and an elongation step at 72° C. for 5 min. The fusion product was subsequently amplified by pfu in the third PCR with the forward primer P9 and the reverse primer P14 (Table 1). This amplicon consisted of 816 bp of upstream sequence of oppA and 930 bp of downstream sequence of oppA flanking the kanamycin cassette. The amplicon was purified from 1% agarose gel with the Qiaquick gel extraction kit (Qiagen, Valencia Calif.) and sent for sequencing at the RPCI DNA sequencing facility.

TABLE 1

Oligonucleotide primer sequences

| Primer | Gene | Experiment | Direction | Sequence[1] |
|---|---|---|---|---|
| P1 | oppA | PCR/sequencing | forward | 5' ATGAAAAAAACGAAGTTATTTG CC 3' (SEQ ID NO: 3) |
| P2 | oppA | PCR | reverse | 5' TCAATTCGCTGTTGTCGTATC 3' (SEQ ID NO: 4) |
| P3 | oppA | RT-PCR | forward | 5' AATCAGGCATCGGTCATCTC 3 (SEQ ID NO: 5)' |
| P4 | oppA | RT-PCR | reverse | 5' TCAGTCGTGATAGGCTGTGC 3 (SEQ ID NO: 6)' |
| P5 | oppA | sequencing | forward | 5' GGGATGCTGACAATGTTC 3' (SEQ ID NO: 7) |
| P6 | oppA | sequencing | forward | 5' 'TGTCATTGAAACCGAGACC 3' (SEQ ID NO: 8) |
| P7 | oppA | cloning | forward | 5' ATC<u>GCCATGG</u>AAGCAATAATAG CACGACA 3' (SEQ ID NO: 9) |
| P8 | oppA | cloning | reverse | 5' GGT<u>CGGATCC</u>ATTCGCTGTTGT CGTATC 3' (SEQ ID NO: 10) |
| P9 | F1/oppAUSG[2] | Overlap extension PCR/colony PCR/sequencing | forward | 5' TCTGACACGCTATCCTCACGAA 3' (SEQ ID NO: 11) |
| P10 | F1/oppAUSG | Overlap extension PCR/colony PCR | reverse | 5' TAGTTAGTCACTTGTGATGCTG TCGTGCTATTAT 3' (SEQ ID NO: 12) |
| P11 | F2/aphA-3 | Overlap extension PCR/colony PCR | forward | 5' GCATCACAA GTGACTAACTAG GAGGAATAAATGG 3' (SEQ ID NO: 13) |
| P12 | F2/aphA-3 | Overlap extension PCR/colony PCR | reverse | 5' GCCATGCTTGCATTATTCCCTC CAGGTACTAAAAC 3' (SEQ ID NO: 14) |
| P13 | F3/oppADSG[3] | Overlap extension PCR/colony PCR | forward | 5' GGGAATAATGCAAGCATGGCA AAGTGAAAAATCG 3' (SEQ ID NO: 15) |
| P14 | F3/oppADSG | Overlap extension PCR/colony PCR | reverse | 5' CACAAGCCCTTCTGGTGATT 3' (SEQ ID NO: 16) |
| P15 | oppA | Colony PCR | forward | 5' AAGACTTTGGGCAAATGGTG 3' (SEQ ID NO: 17) |
| P16 | oppA | Colony PCR | reverse | 5' TCAGTCGTGATAGGCTGTGC 3' (SEQ ID NO: 18) |
| P17 | oppAUSG/F1 | sequencing | forward | 5' AAGGAGAAGTAGCAAGGAGG 3' (SEQ ID NO: 19) |
| P18 | aphA-3/F2 | sequencing | forward | 5' GAAGATGAACAAAGCCCTG 3' (SEQ ID NO: 20) |
| P19 | oppADSG/F3 | sequencing | forward | 5' ACACTTTTACCGCCTTGG 3' (SEQ ID NO: 21) |

[1]Restriction enzyme sites are underlined. Overlapping regions are shown in bold. Extended sequences complementary to the end of the adjacent gene are shown in italics.
[2]USG: upstream gene
[3]DSG: downstream gene.

Mutant Construction.

The isogenic oppA mutant strain was constructed by transformation of *M. catarrhalis* strain 035E with the overlap extension PCR product. Briefly, strain 035E was grown to $OD_{600\,nm}$ at 0.2. A volume of 100 µl of the bacterial culture was then spread on BHI agar plate and air dried. Two circles (2 cm diameter) were marked on the plate. Either 30 µl distilled water or 30 µl of water containing 100 ng of DNA was dropped onto these circles, followed by incubation at 37° C. with 5% $CO_2$ for 5 h. Bacteria within each circle were harvested with a cotton swab and spread on BHI plates containing 50 µg/ml kanamycin. After 24 h incubation at 37° C. with 5% $CO_2$, numerous colonies were present on the selection plate following DNA transformation but no visible colony was present on the water control plate. The mutant colonies were examined by PCR and sequencing as described in Results.

Cloning of the oppA Gene.

The pCATCH plasmid is an expression vector engineered to express recombinant lipoprotein and has been used previously to express *M. catarrhalis* lipoproteins. The 1967 bp oppA gene encoding the mature OppA protein was amplified from *M. catarrhalis* strain ATCC 43617 with primers P7 and P8 (Table 1) and ligated into pCATCH between restriction sites NcoI and BamHI. The ligation mixture was transformed into chemically competent *E. coli* Top10 strain and grown on kanamycin (50 µg/ml) selection plate. The OppA expression plasmid was named pCATCH/OppA.

Southern Blot Assay.

Southern blot assays were performed with genomic DNA that was restricted with PvuII and NdeI using a Hoefer TransVac vacuum blotting unit following the manufacturer's instructions (Hoefer, San Francisco, Calif.). Probes were biotinylated with an NEBlot Phototope-Star detection kit (New England Biolabs) according to the manufacturer's instructions.

Expression and Purification of His-OppA Protein.

pCATCH/OppA was transformed into *E. coli* BL21(DE3) strain to express OppA as a lipoprotein with a thrombin cleavable C-terminal hexahistidine tag. A volume of 500 ml LB broth containing 50 µg/ml kanamycin was inoculated with 20 ml overnight culture of bacteria harboring the expression vector. Following growth to $OD_{600\,nm}$ of 0.6, OppA expression was induced with 3 mM IPTG for 4 hours at 37° C. The bacteria were then harvested by centrifugation at 4,000 g for 15 min at 4° C. The pellet was suspended in 10 ml of lysis buffer (20 mM sodium phosphate, 500 mM NaCl, 1 mg/ml lysozyme, 100 µg/ml PEFABLOC (Roche, Indianapolis, Ind.), pH 7.4) and mixed with a nutator for 30 min at 4° C. The suspension was then sonicated with a Branson Sonifier 450 at setting 6, using 80% pulsed cycle of 4×30 sec bursts with 2 min pauses. The sonicated bacterial lysate was centrifuged at 10,000 g for 20 min at 4° C. The supernatant containing His-OppA protein was saved for protein purification.

His-OppA was purified with Talon metal affinity resin (BD Biosciences, Palo Alto, Calif.) following the manufacturer's instructions. Two ml of 50% suspension of the Talon resin was loaded to a 20 ml chromatography column. The resin storage buffer was drained and the remaining 1 ml beads were equilibrated with 2×10 ml binding buffer (20 mM sodium phosphate, 500 mM NaCl, PH 7.4). After equilibration, the Talon beads were incubated with 10 ml of bacterial supernatant in the column with both ends capped for 20 min at room temperature with rocking. The unbound protein was drained and the bound protein was washed with 2×20 ml wash buffer (20 mM sodium phosphate, 500 mM NaCl, 10 mM imidazole, 10 mM beta-mercaptoethanol, pH 7.4) and eluted with 5 ml elution buffer (20 mM sodium phosphate, 500 mM NaCl, 150 mM imidazole, pH 7.4) by gravity flow. The eluates were collected every 500 µl in each tube. Tubes containing concentrated protein fractions were pooled and subject to buffer exchange into phosphate buffered saline (PBS) by using a Centricon YM-10 filter device (Millipore corporation, Danvers, Mass.). The concentration of the purified protein was determined by bicinchoninic acid assay (Pierce, Rockford, Ill.). The quality of the purified protein was examined by SDS-PAGE and Coomassie blue stain.

Development of Antisera to OppA and Whole Bacteria.

Purified recombinant His-OppA protein was sent to Covance (Denva, Pa.) for antibody production in New Zealand White rabbits using a 118-day protocol. Briefly, 250 µg purified OppA was emulsified 1:1 in complete Freund's adjuvant for initial subcutaneous injection. Subsequent immunizations followed a three-week cycle of boosts with 125 µg OppA emulsified 1:1 in incomplete Freund's adjuvant. Test bleeds were taken approximately 10 days after the boosts. Final bleeds were taken 2 weeks after the 5$^{th}$ boosts.

Rabbit anti-035E antisera was obtained from Covance as follows. New Zealand White rabbits were injected subcutaneously and intramuscularly twice with a 4-week interval with $10^9$ colony forming units of *M. catarrhalis* 035E emulsified with incomplete Freund's adjuvant (1:1). Blood samples were collected 2 weeks after the final injection. Rabbit antiserum to OMP CD was produced in our laboratory.

SDS-PAGE and Immunoblot Assay.

Whole cell extracts of *M. catarrhalis* clinical strains, 035E and the 035E/oppA mutant were prepared by suspending a loop of bacterial colonies grown on the BHI agar plates in 100 µl PBS. The bacterial suspension was then mixed with 100 µl 2×SDS-PAGE sample buffer (Laemmli buffer) and boiled for 10 min. Twenty µl of each whole cell extract was separated on 10% SDS-PAGE gel and transferred to nitrocellulose membrane.

For immunoblot assay with the rabbit anti-035E antiserum, the membrane was incubated with 1:5000 dilution of the primary antibody in TBST (20 mM Tris-HCl, 150 mM NaCl, 0.1% TWEEN-20, pH 7.5) followed by 1:2000 dilution of the peroxidase labeled goat anti-rabbit IgG antibody (KPL, Gaithersburg, Md.) in TBST as secondary antibody. Bands were detected by using the SuperSignal West Pico Chemiluminescence kit (Thermo Fisher Scientific Inc, Rockford, Ill.). The image was acquired with an AlphaImager (Alpha Innotech corporation, San Leandro, Calif.).

For immunoblot with the rabbit anti-OppA or anti-CD antibody, primary antibodies used were 1:2000 dilution of test bleed anti-OppA antiserum, 1:15,000 dilution of final bleed anti-OppA antiserum, and 1:2000 dilution of anti-CD antiserum. A 1:2000 dilution of the peroxidase labeled goat anti-rabbit IgG antibody was the secondary antibody followed by colorimetric detection.

For immunoblot with the mouse antisera pooled following mucosal immunization with recombinant OppA protein, *M. catarrhalis* 035E, or PBS control, the membranes were incubated with 1:10,000 dilution of the antisera and probed with 1:25,000 dilution of peroxidase conjugated anti-mouse IgG and developed with chemiluminescence.

Serum from Adults with COPD.

Serum samples were obtained from adults enrolled in our COPD Study Clinic at the Buffalo Veterans Affairs Medical Center. Patients were seen monthly and at times when an exacerbation was suspected. At each visit, serum and expectorated sputum samples were collected and bacteria present in the sputum were identified. Serum samples collected ~1 month before (pre acquisition) and ~1 month after (post clearance) acquisition and clearance of *M. catarrhalis* were subjected to whole cell ELISA assays to analyze the human systemic immune response to *M. catarrhalis* infection. Nineteen pairs of serum samples with a positive response to homologous infecting strains were used in ELISA assays with purified recombinant OppA protein in this study to examine the OppA specific antibody response. Eight pairs of serum samples collected two months apart from patients who never had positive sputum culture for *M. catarrhalis* during the study were used as negative controls.

ELISA.

ELISA was carried out by coating the wells of a 96-well microtiter IMMUNOLON 4 plate (Thermo Labsystems, Franklin, Mass.) with 500 ng of purified recombinant His-OppA protein overnight in coating buffer (0.1M $Na_2CO_3$ and 0.1 M $NaHCO_3$, pH 9.6). Equal volumes of coating buffer were added to control wells for each well that received OppA. The plate was washed once with PBST (0.5% TWEEN-20 in PBS buffer) and blocked with 3% BSA (bovine serum albumin) in PBS for 1 h at room temperature, after which the plate was washed once again with PBST. Paired COPD patient sera (pre acquisition and post clearance) described above were diluted 1:2,000 in diluent buffer (1% BSA in PBST) and added to the sham coated control wells and His-OppA coated sample wells in parallel. After incubation for 1 h at room temperature, plate was washed 4 times with PBST and 1:6000 dilution of peroxidase labeled secondary antibody, goat anti-human IgG (KPL, Gaithersburg, Md.) was added. After another 1 h incubation the plate was washed 5 times with PBST and developing reagent was added to the wells. The reaction was allowed in the dark for 10 min and stopped with 2M sulfuric acid. The absorbance at 450 nm was determined using a Bio-Rad model 3550-UV microplate reader.

The OD value of the sham coated control wells was subtracted from the OD value of each corresponding sample well to give a normalized OD of each sample. The percentage change in the normalized OD between paired samples were calculated with the following formula: (OD post clearance sample−OD pre acquisition sample)/OD pre acquisition sample)×100. ELISAs were repeated in four independent experiments. The percentage change in OD of each paired sample was determined as the average of the values derived from the four experiments. The mean and standard deviation (SD) of the percentage change of control sera were calculated. The cutoff for a significant percentage change of the sample sera was set as (Mean+2 SD) of percentage change of controls.

Whole Cell ELISA. *M. catarrhalis* strain 035E and the 035E/oppA mutant strain were grown in BHI broth to $OD_{600\,nm}$ at 0.2, harvested by centrifugation and resuspended in PBS. A volume of 100 µl of the suspension was added to each well of the 96-well microtiter IMMUNOLON 4 plate (Thermo Labsystems, Franklin, Mass.). Wells with PBS alone were included as controls. The rest of the experiment was performed following the protocol described above for ELISA with OppA. Primary antibodies, either rabbit anti-OppA antibody, rabbit anti-CD antibody (positive control) or rabbit anti protein 140, a non surface exposed protein (negative control) diluted in 2 fold serial dilutions from 1:10,000 to 1:40,000, were added to the wells. Secondary antibody was 1:4000 dilution of peroxidase labeled goat anti rabbit IgG (KPL, Gaithersburg, Md.).

Flow Cytometry.

*M. catarrhalis* was grown to mid-logarithmic phase and 100 µl of culture was centrifuged at 4000×g for 5 minutes. The bacterial pellet was resuspended in an appropriate dilution of heat inactivated (56° C. for 30 minutes) rabbit serum in PBS. Appropriate dilutions were determined by performing initial experiments at multiple two-fold dilutions to identify the dilution of serum that yielded the greatest signal to noise ratio. Two negative controls were included: 1) bacteria incubated in PBS alone and 2) bacteria incubated with rabbit antiserum directed at a non surface protein 140. Bacteria incubated with polyclonal antiserum from rabbits immunized with whole bacterial cells were used as a positive control. Bacteria were incubated with antisera for 1 hour at 37° C. The bacteria were washed with PBS and resuspended in a 1:10 dilution of antibody conjugated to flourescein isothiocyanate (KPL). After 30 minutes of incubation at 37° C., the sample was diluted with 900 µl PBS and fluorescence was detected with a FACSCalibur flow cytometer using Cell Quest 3.1 software (BD Biosciences, San Jose, Calif.).

Mucosal Immunization of Mice.

Groups of six Balb/c mice were immunized intranasally with either 50 µg purified recombinant OppA plus 1 µg cholera toxin, or formalin-killed *M. catarrhalis* 035E plus 1 µg cholera toxin, or 1 µg cholera toxin alone in PBS buffer as a sham immunization control. Intranasal immunization was performed on days 0, 10 and 20 by placing a pipette tip with 5 µl immunogen at each nostril of a conscious mouse to sniff. Immunized mice were challenged on day 28 as described below.

Mouse Pulmonary Clearance Model.

The mouse pulmonary clearance model was used. Overnight culture of *M. catarrhalis* 035E was inoculated into 100 ml BHI broth with $OD_{600}$ of 0.05 and grown to an $OD_{600}$ of 0.3. Bacteria were collected by centrifugation and resuspended in 10 ml PCGM buffer (4.3 mM $NaHPO_4$, 1.4 mM $KH_2PO_4$, 137 mM NaCl, 2.7 mM KCl, 5 mM $CaCl_2$, 0.5 mM $MgCl_2$, 0.1% gelatin, pH 7.3). An aliquot of suspension was diluted and plated to determine the starting concentration of bacteria which was approximately $1\times10^9$ colony forming units per ml in each experiment. Ten ml of the bacterial suspension was placed in the nebulizer of a Glas-Col Inhalational Exposure System model 099C A4212 (Glas-Col, Terre Haute, Ind.). Immunized mice were challenged using this inhalation system with the following settings: 10 min preheat, 40 min nebulization, 30 min cloud decay, 10 min decontamination, vacuum flow meter at 60 cubic feet/h, compressed air flow meter at 10 cubic feet/h.

Three hours post-challenge, the mice were anesthetized by inhalation of isoflurane and bled by retro-orbital puncture. Serum was heat inactivated at 56° C. for 30 min and stored at −20° C. for later use. After serum was collected, the anesthetized mouse was euthanized by administration of additional isoflurane. Lungs were then harvested and homogenized on ice in 5 ml PCGM buffer using a tissue homogenizer. Aliquots 20 µl of undiluted and 1:10 diluted lung homogenate were plated in duplicate and incubated at 35° C. with 5% $CO_2$ overnight. Colonies were counted the following day. Statistical significance of colony counts between groups of immunized and sham-immunized mice was determined by two-tailed t-tests. A p value of <0.05 was considered significant.

Results

Identification and Characterization of the oppA Gene.

The genomic sequence of *M. catarrhalis* strain ATCC 43617 was available as 41 contigs in GenBank (accession numbers AX067426 to AX067466). Computer programs predicted approximately 1,800 ORFs in the genome. These ORFs were analyzed previously in our laboratory to identify putative surface proteins as vaccine candidates leading to the identification of the oppA gene on contig 34 (AX067459, gi12545079) and was predicted to encode a lipoprotein. Homolog analysis by NCBI blastn search using the full-length sequence of the oppA gene revealed significant homology of this gene to the oppA genes in Streptococcus pyogenes strains with approximately 69% identities and 83% similarities.

The oppA gene is the last ORF in a cluster of five being translated in the same frame. The four ORFs preceding oppA gene exhibited significant homologies to the oppB, oppC, oppD, and oppF genes of S. pyogenes, respectively. Specifically, the identities of these genes between M. catarrhalis ATCC43617 (AX067459, gi12545079) and a S. pyogenes strain (X89237, gi1420857) are 68.5% for oppB, 75% for oppC, 70.8% for oppD, and 69.2% for oppF. The organization of these five genes in both strains is depicted in FIG. 1A with nucleotide positions referring to their location in the Genbank sequence. Generally, the five genes encoding the five proteins of the oligopeptide transport system are organized in an operon except for additional copies of the oppA gene, if present. Consistent with this observation, the oppA gene of M. catarrhalis is present in the immediate vicinity of the other oligopeptide transporter genes, presumably constituting a single operon. Interestingly, although all five genes from M. catarrhalis showed significant homologies to corresponding genes from S. pyogenes, the organization of these five genes is different in these two bacterial species with the oppA genes located in opposite extremities of the operon. This may be of significance in terms of messenger RNA stability in different intracellular environments of the organisms where multiple mechanisms of mRNA inactivation are present.

Bacteria carry from 2 to 5 copies of oppA genes in their genome. However, a blast search of a database containing genome sequences of 5 M. catarrhalis strains including ATCC43617, 7169, 46P47B1, 103P14B1, and 12P80B1 identified only a single oppA gene. This database is accessible at the NCBI website: //camp.mic.med.buffalo.edu/blast/blast_cs.html. Similarly, only a single oppA gene in present in the two strains of M. catarrhalis whose genomes are published (ATCC 43617 and RH4).

Figure 2:
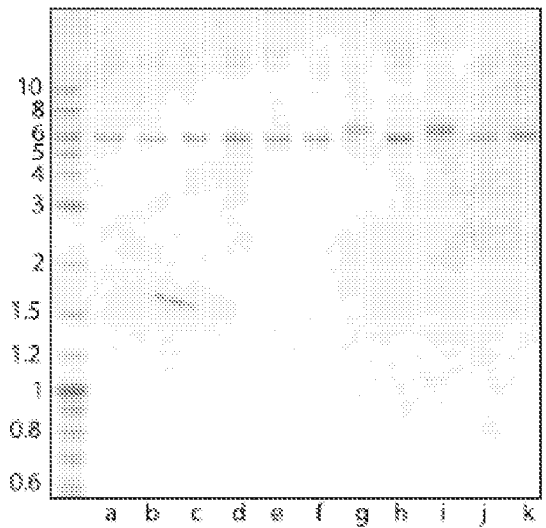
FIG. 2. Southern blot assay. Purified genomic DNA of *M. catarrhalis* strains was restricted with PvuII and NdeI and hybridized with a 200 bp probe corresponding to oppA. Lanes a, O35E. Lanes b through f contain otitis media strains b, 135; c, 555; d, 3584; e, 5488; f, 6952. Lanes g through k contain COPD strains g, 6P29B1; h, 29P24B1; 1,33P25B2; j, 55P18B3; k, 96P9B1. Molecular size markers are noted on the left in kilobases.

To further evaluate whether strains of M. catarrhalis have one or more copies of the oppA gene, a Southern blot assay was performed with 10 clinical isolates including 5 middle ear fluid isolates that caused otitis media and 5 isolates from the sputum of adults with COPD. A single band is observed in each strain (FIG. 2). Eight strains have a band of identical size whereas two strains have bands that are slightly larger. Thus we conclude that strains of M. catarrhalis have a single oppA gene based on 1) analysis of genome sequences of 7 strains, 2) results of PCR with 20 strains (See FIG. 1B and below) and Southern blot assay (FIG. 2).

In bacteria carrying multiple copies of oppA genes, the oppA copies are generally not identical and the OppA proteins play both redundant and unique physiological roles. This would intuitively increase the complexity of OppA based vaccine development for that species, if applicable. A single copy of the oppA gene in M. catarrhalis was therefore considered an appealing feature in our study on vaccine investigation.

Sequence Conservation of oppA Among Strains.

The oppA gene was evaluated for sequence conservation among M. catarrhalis strains in 10 sputum isolates from adults with COPD and 10 middle ear fluid isolates from children with otitis media. The 2039 bp full length oppA genes were amplified by PCR with primers P1 and P2 (Table 1) from these 20 strains and the ATCC 43617 strain as a positive control. A single band of the expected size was present in each strain (FIG. 1B, suggesting that the oppA gene is present and similar in gene length among M. catarrhalis strains.

In order to examine the sequence conservation of the oppA gene, PCR products from the 20 clinical isolates and the ATCC 43617 strain were purified and sequenced. Nucleotide sequences and translated amino acid sequences were aligned with the MacVector program by which the oppA homology among these strains was calculated. The results showed that the DNA sequence of the PCR product from ATCC 43617 were identical to the oppA gene sequence in GenBank, which validated the sequence information derived from our PCR products. Overall, a small number of nucleotide variations were present in each strain. The nucleotide variations collected from all strains were distributed at 18 discrete and consecutive nucleotide positions scattered over the 2039 bases full length oppA gene. Nucleotide variations at 12 of these positions were silent and those at the other 6 positions gave rise to 3 amino acid changes. The gene identity scores among these strains range from 98.7%-100%. These data indicate that oppA gene is highly conserved among M. catarrhalis strains.

Of interest, sequence analysis revealed that nucleotide variations occurring at 10 of 18 positions were found exclusively in sputum isolates, whereas nucleotide variations occurring at another 5 sites were found exclusively in middle ear fluid isolates. The nucleotide variations at the remaining 3 positions were present in strains of both clinical sources. This observation suggests that while oppA varies slightly in adaptation to a different environmental niche, the gene is even more conserved within a specific ecological group of strains.

Transcription of the oppA Gene.

Once sequence conservation of the oppA gene was confirmed we examined if the oppA gene is transcribed in M. catarrhalis. M. catarrhalis 035E strain was originally isolated from the middle ear fluid of a patient with otitis media in Dallas and was subsequently widely used in M. catarrhalis studies. RT-PCR for oppA gene expression was performed with total RNA extracted from this strain. A 223 bp fragment within the oppA gene was amplified by PCR with P3 and P4 primers (Table 1), using genomic DNA extracted from 035E as template (FIG. 1C, lane 4). A DNA product of the same length was produced by RT-PCR (lane 2), which is, however, absent in the negative control lacking the reverse transcriptase (lane 3). This result indicated that the oppA gene is transcribed in M catarrhalis strain 035E.

Recombinant His-OppA Protein.

The M. catarrhalis oppA gene encodes a predicted lipoprotein with a 23 amino acid signal peptide at the amino terminus, which contains a consensus lipoprotein signal peptidase (LSP) recognition site, LAAC. The mature OppA protein after LSP cleavage consists of 656 amino acids. The oppA gene region encoding the mature OppA protein was inserted into pCATCH vector to express recombinant OppA as a lipoprotein with a C-terminal hexahistidine tag in E. coli BL21(DE3) as described in Materials and Methods. A COOMASSIE stained SDS-PAGE gel (FIG. 3A) shows that the recombinant His-OppA protein (~85 kD) is present in the bacterial lysate following induction with IPTG (lane 2) and it was retained in the supernatant of the lysate as a soluble protein after sonication (lane 3). Following affinity purification with the Talon metal affinity resin, the recombinant protein was purified to over 95% purity (lane 4) and stored in PBS for other applications.

Characterization of oppA Mutant.

Figure 4:
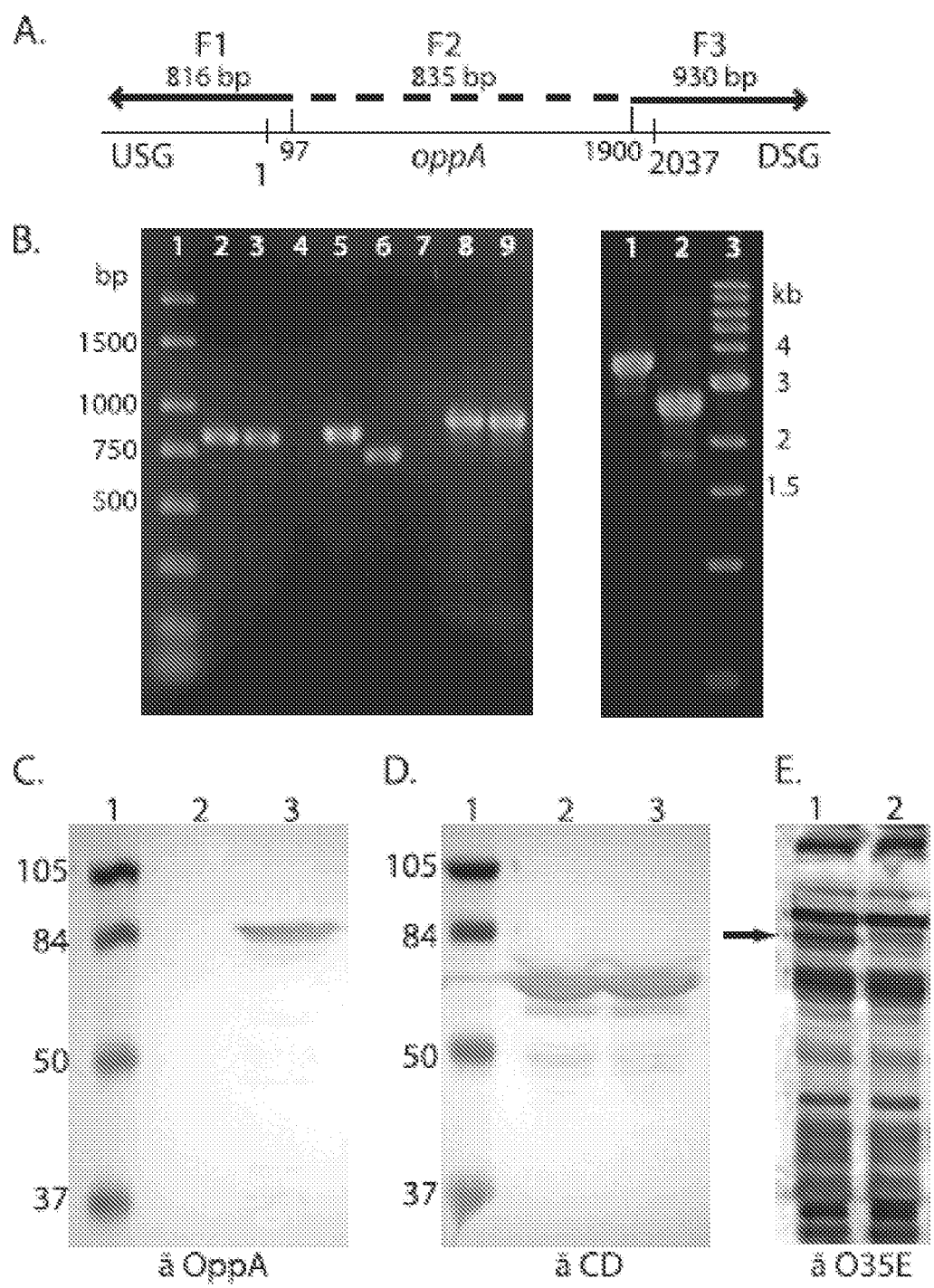
FIG. 4. Construction and characterization of the isogenic oppA mutant *M. catarrhalis* 035E strain. The oppA gene (from nt 97 to 1900) was replaced by the kanamycin resistance gene via homologous recombination in the oppA mutant. A: Schematic depiction of the transforming DNA fragment in relation to the oppA gene in the genome. Numbers under the line indicate the nucleotide position within the oppA gene. USG: upstream gene; DSG: downstream gene. B: Paired PCRs to examine the targeted mutagenesis in the oppA mutant as compared to the wild type. Left panel: lane 1, DNA standards; Lane 2 and 3, PCR of the F1 fragment; Lane 4 and 5, PCR of the F2 fragment; Lane 6 and 7, PCR of a region (nt 1073-1811) of the oppA gene; Lane 8 and 9, PCR of the F3 fragment. Lane 2, 4, 6, and 8, PCR with the wild type DNA as template; lane 3, 5, 7, and 9, PCR with the oppA mutant DNA as template. Right panel: PCR of the whole region of genes involved in the mutagenesis with the forward primer of F1 and the reverse primer of F3. Lane 1, PCR with the wild type DNA as template; lane 2, PCR with the mutant DNA as template; lane 3, DNA standards noted in kilobases. Panels C and D: Immunoblot assays of whole cell lysates of the wild type *M. catarrhalis* 035E and the oppA mutant. Panel C: Immunoblot with rabbit anti-OppA antibody. Panel D: Immunoblot with rabbit anti-CD antibody. Lanes 1, protein standards (kilodaltons); lanes 2, whole cell lysate of the oppA mutant; lanes 3, whole cell lysate of wild type O35E. Panel E: Immunoblot assay with rabbit antiserum raised to whole cells of *M. catarrhalis* 035E. Lane 1, whole cell lysate of the wild type; lane 2, whole cell lysate of the oppA mutant. Arrow denotes OppA protein in wild type strain.

The isogenic oppA mutant 035E strain was constructed by replacing the oppA gene with a nonpolar kanamycin resistance cassette via homologous recombination. The region of mutagenesis is illustrated in FIG. 4A. A 97 bp sequence at the 5' end and a 137 bp sequence at the 3' end of the oppA gene were retained in the mutant strain as a result of optimal primer designs for the overlap extension PCR. After transformation of the O35E strain with the purified PCR product, the resulting mutagenesis was confirmed by PCR of the wild type and the mutant strains. An 816 bp F1 fragment and a 930 bp F3 fragment were present in both strains while the 835 bp F2 was present only in the mutant strain and a 739 bp oppA gene fragment was present only in the wild type (WT) strain (FIG. 4B left panel). PCR with the forward primer of F1 and the reverse primer of F3 gave rise to a 3526 bp amplicon from the WT strain and a 2541 bp amplicon from the mutant strain, as expected (FIG. 4B right panel). Sequences of these two amplicons confirmed that the targeted oppA gene was knocked out in the mutant strain while the upstream and downstream genes flanking oppA were completely preserved.

OppA Expression in *M. catarrhalis* Strain O35E.

Rabbit anti-OppA antibody was raised against purified recombinant OppA as described in Materials and Methods. This antibody was used in immunoblot analysis to examine the expression of OppA in *M. catarrhalis*. The immunoblot assay was performed with whole cell extracts of both WT and oppA mutant O35E strain. OMP CD is a constitutively expressed *M. catarrhalis* protein; antiserum to OMP CD was used as a protein expression control in the assay. Antibodies raised to recombinant OppA specifically recognized the OppA protein from the whole cell extracts of the WT strain; the band is absent in the whole cell extracts of the mutant strain (FIG. 4C). The anti-CD antibody recognized OMP CD from the whole cell extracts of both strains (FIG. 4D). We conclude that the native OppA protein is recognized by the rabbit anti-OppA antibody raised to purified recombinant OppA. The results also indicate that OppA is expressed in *M. catarrhalis* O35E during growth in vitro while the protein is absent in the oppA mutant strain.

Immunogenicity of the OppA Protein.

In order to further evaluate OppA as a vaccine antigen, we characterized the immunogenicity of the OppA protein in *M. catarrhalis*. First, we assessed if the native OppA protein is immunogenic in a mammalian host presented with the whole organism. To answer this question, rabbit antiserum was raised against the whole organism of *M. catarrhalis* O35E and the presence of antibodies to OppA in the rabbit antiserum was examined by immunoblot assay.

Whole cell extracts of the O35E WT and oppA mutant strains were separated by SDS-PAGE and subjected to immunoblot assay with the rabbit anti-O35E antiserum. A band of ~84 kD was present in the WT strain but absent in the mutant strain (FIG. 4E). These data suggest that rabbit antiserum raised to whole bacterial cells of strain O35E contains antibodies that bind OppA. Therefore, we conclude that native OppA protein is an immunogenic protein in *M. catarrhalis*.

Figure 3:
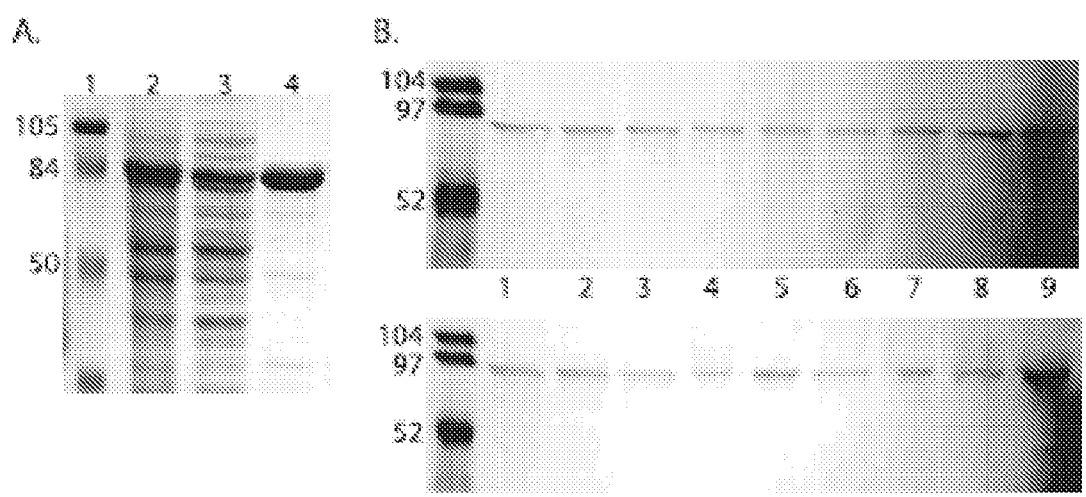
FIG. 3. Panel A. Coomassie blue stained SDS gel of His-OppA purification products. *E. coli* BL21(DE3) harboring the His-OppA expression plasmid, pCATCH-OppA, was induced by 3 mM IPTG for 4 h, the whole bacterial cell lysate was extracted and subjected to sonication. After centrifugation, the clarified supernatant was incubated with Talon metal affinity resin and His-OppA was eluted with imidazole. Lane 1, protein standards (kilodaltons); Lane 2, whole bacterial cell lysate following IPTG induction; lane 3, supernatant containing His-OppA; lane 4, purified His-OppA. Panel B. Immunoblot assays with rabbit anti-OppA antiserum. Whole cell lysates of clinical isolates of *M. catarrhalis* assayed with rabbit antiserum raised to purified recombinant (1:15,000 dilution) OppA. Blots were probed with peroxidase conjugated goat anti-rabbit IgG (1:2000 dilution) and developed with horseradish peroxidase color developer. Lane 1, molecular mass marker (kilodaltons). Lanes 2-9, upper panel contain whole cell lysates of middle ear fluid isolates 155, 238, 555, 2910, 3584, 3614, 5488, 6952. Lanes 2 through 9, lower panel contain whole cell lysates of COPD sputum isolates 5P34B1, 10P58B2, 12P15B2, 29P24B1, 33P25B2, 39P29B2, 55P18B3, 63P62B1.

To determine whether antibodies raised by immunization with recombinant OppA recognized epitopes on OppA of multiple strains of *M. catarrhalis*, immunoblot assays were performed with rabbit antiserum to recombinant OppA. FIG. 3B shows that rabbit antiserum raised to recombinant OppA recognized a single band in whole bacterial cell lysates corresponding to the size of OppA. The band was present in 8 of 8 middle ear fluid isolates from children with otitis media and 8 of 8 sputum isolates from adults with COPD. We conclude that immunization with recombinant OppA induces antibodies that bind native OppA in multiple strains of *M. catarrhalis*.

Human Systemic Antibody Response to OppA.

We next assessed if OppA is an antigenic protein of *M. catarrhalis* during infection of the human respiratory tract. Immunoassays with convalescent patient serum can not only identify antigenic proteins expressed during infection to a level sufficient to induce immune responses, but also indicate possible bacterial targets of the host immune system. To examine whether or not OppA is expressed by *M. catarrhalis* during infection in adults with COPD and induces an immune response, ELISAs were performed to measure the serum IgG response to OppA following *M. catarrhalis* infection.

ELISA was performed to measure antibodies to OppA in 19 pairs of patient serum samples (pre acquisition and post clearance) and 8 pairs of negative control samples as described in Materials and Methods. The percentage change in OD between paired samples was calculated. The mean and SD value for negative controls were −3.44% and 15.98%, respectively, representing a nonspecific percentage change distribution with an upper limit of 28.52% (mean+2SD) with 99% confidence. Therefore any percentage change in paired pre acquisition to post clearance serum samples greater than 28.52% can be regarded as significant. According to this criterion, none of the 19 pairs of patient serum samples demonstrated significant percentage change. However, all serum samples including our negative controls have high levels of anti-OppA activity when tested with the purified recombinant OppA protein in ELISAs. Two pairs of serum samples were arbitrarily selected to titrate the anti-OppA level. Both gave titers over 1:10,000, which was defined by the highest dilution of the serum in OppA coated wells giving an OD value 3 fold greater than that derived from the corresponding sham coated control wells. Based on the results of these assays, we speculate that the preexisting high level of antibody to OppA most likely masked any possible anti-OppA immune response, if present, following an episode of *M. catarrhalis* infection.

Surface Exposure of OppA Epitopes.

Figure 5:
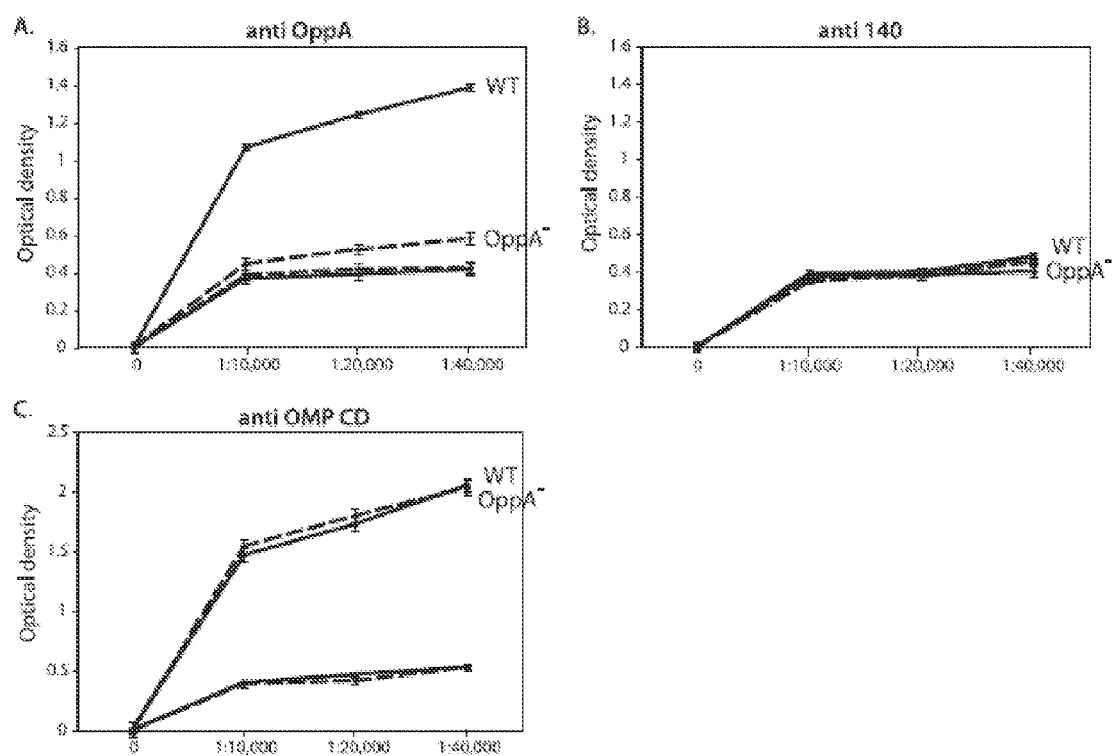
FIG. 5. Results of whole cell ELISA with *M. catarrhalis* 035E wild type (WT, solid lines) and the oppA mutant (OppA⁻, dotted lines). X-axes are dilutions of serum and Y-axes are optical density at 450 nm. Wells were incubated with rabbit anti-OppA (panel A), rabbit anti-140, a non surface protein (panel B) and rabbit anti-OMP CD a known surface protein (panel C). Corresponding pre bleed sera from rabbits were tested simultaneously as controls. Error bars indicate standard deviation of triplicate values. Curves with solid lines indicate results with wild type and curves with dotted lines indicate results with the OppA⁻ mutant.

Whole cell ELISA. Surface exposure is an important property of vaccine antigens. Whole cell ELISA was performed to examine the surface exposure of OppA epitopes on *M. catarrhalis*. OMP CD is a surfaced exposed *M. catarrhalis* protein used as a control. Microtiter wells coated with both WT and oppA mutant O35E strains were incubated with the anti-OppA, anti-CD and anti protein 140 (non surface protein) antisera in ELISA. Anti-OppA antibody was captured by the WT strain but not by the oppA mutant strain (FIG. 5), while anti-CD antibody (positive control) was captured by both strains, and anti 140 antibodies (negative control) were captured by neither strain. This result indicates that cells of the oppA mutant strain lack affinity for the anti-OppA antibody and the binding of anti-OppA antibody to cells of the WT strain was specifically mediated by OppA protein. We conclude that the OppA protein has epitopes on the bacterial surface and these epitopes are accessible to antibody binding. This characteristic suggests that OppA has potential as a protective immunogen.

Flow Cytometry.

Figure 6:
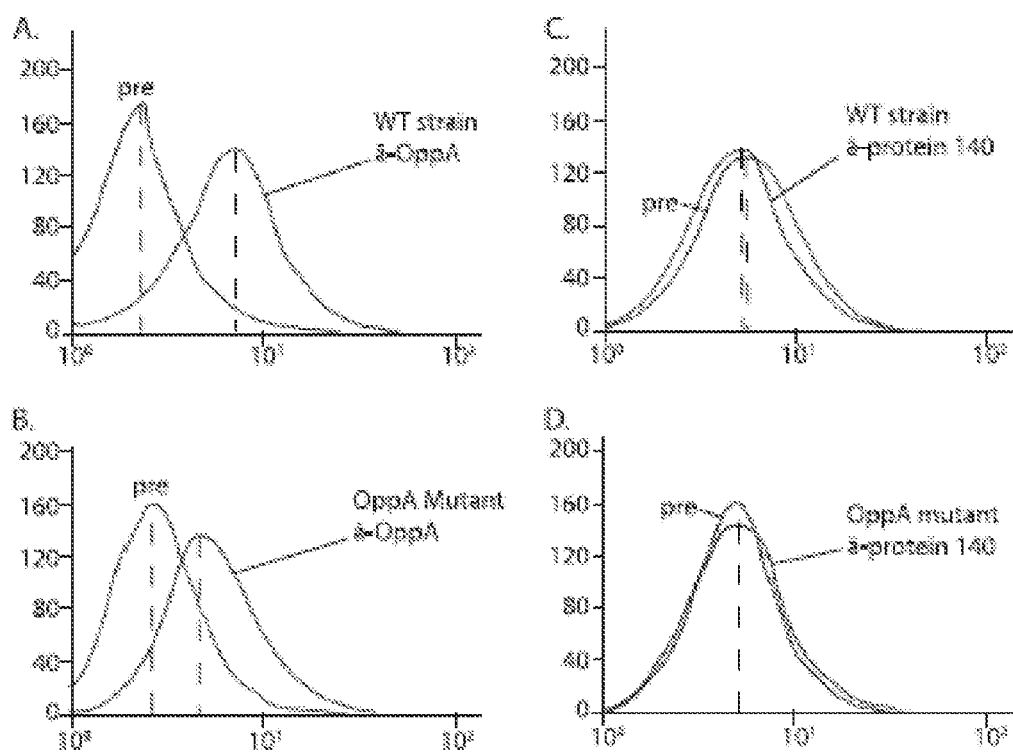
FIG. 6. Results of flow cytometry with *M. catarrhalis* wild type 035E and OppA mutant. X-axes are fluorescence and Y-axes are cell counts. A. Wild type strain 035E assayed with rabbit antiserum to recombinant purified OppA (1:400) and preimmune serum (1:400). B. OppA mutant assayed with rabbit antiserum to recombinant purified OppA (1:400) and preimmune serum (1:400). C. Wild type strain 035E assayed with rabbit antiserum to recombinant purified protein 140, a non surface exposed *M. catarrhalis* protein (1:200) and pre immune serum (1:200). D. OppA mutant assayed with rabbit antiserum to recombinant purified protein 140 (1:200) and preimmune serum (1:200).

As a second independent method to assess the exposure of OppA epitopes on the bacterial surface, antiserum raised to recombinant purified OppA was subjected to flow cytometry with wild type O35E and OppA mutant bacteria. Rabbit antiserum raised to OppA demonstrates an increase in median fluorescence intensity from preimmune serum to immune serum with strain O35E as indicated by a shift of the curve to the right (FIG. 6A). Assaying the same antisera to the OppA mutant (FIG. 6B) show a distinctly less prominent shift to the right from the pre immune to the immune serum, indicating that the OppA immune serum contains OppA-specific antibodies to epitopes on the bacterial surface. FIGS. 6C and 6D shows absent binding of surface epitopes to the wild type and OppA mutant strains with antiserum to protein 140, a non surface exposed protein. The experiment depicted in FIG. 6 was performed three times and yielded similar results each time.

Elution of Antibodies from the Bacterial Surface.

Figure 8:
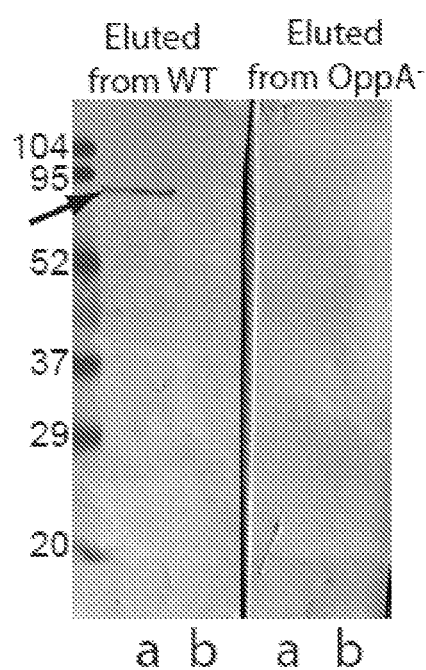
FIG. 8. Immunoblot assays of antibodies eluted from the surface of wild type *M. catarrhalis* (left lane) and OppA mutant (right lane). Lanes contain whole cell lysates.

Intact log phase *M. catarrhalis* cells were incubated with heat inactivated antiserum to OppA to allow antibodies to bind to the bacterial cells. After washing, antibodies were eluted from the surface and tested in immunoblot assay with WT, OppA mutant and purified recombinant OppA (FIG. 8). Antibodies eluted from the bacterial surface specifically recognized OppA, including in multiple clinical isolates. To assess the possibility that cells were sloughing outer membrane or otherwise exposing buried epitopes, the same experiment was performed with cells that were fixed with glutaldehyde and washed thoroughly to stabilize the outer membrane. The same result was obtained.

Based on the results of whole cell ELISAs, flow cytometry and elution of OppA antibodies from the cell surface, we conclude that OppA expresses epitopes on the surface of the bacterial cell. This was a surprising result given the prediction of OppA as a periplasmic protein.

Protective Immune Response.

To determine if mucosal immunization with OppA induces protective immunity against *M. catarrhalis* infection in vivo, the mouse pulmonary clearance model was performed in which groups of mice were immunized intranasally with recombinant purified OppA. Parallel groups of mice were immunized simultaneously with either formalin-killed *M. catarrhalis* 035E as positive control or PBS as negative control. Mice were challenged with live *M. catarrhalis* 035E by an inhalation system on Day 28 post immunization. Three hours post-challenge, the lungs of mice were harvested and bacteria recovered from the lungs were quantified as colony counts. Protective immunity was evaluated as reduced number of colony counts in the OppA immunization group as compared to negative the control group. Statistical significance was analyzed by two-tailed t-tests.

Figure 7:
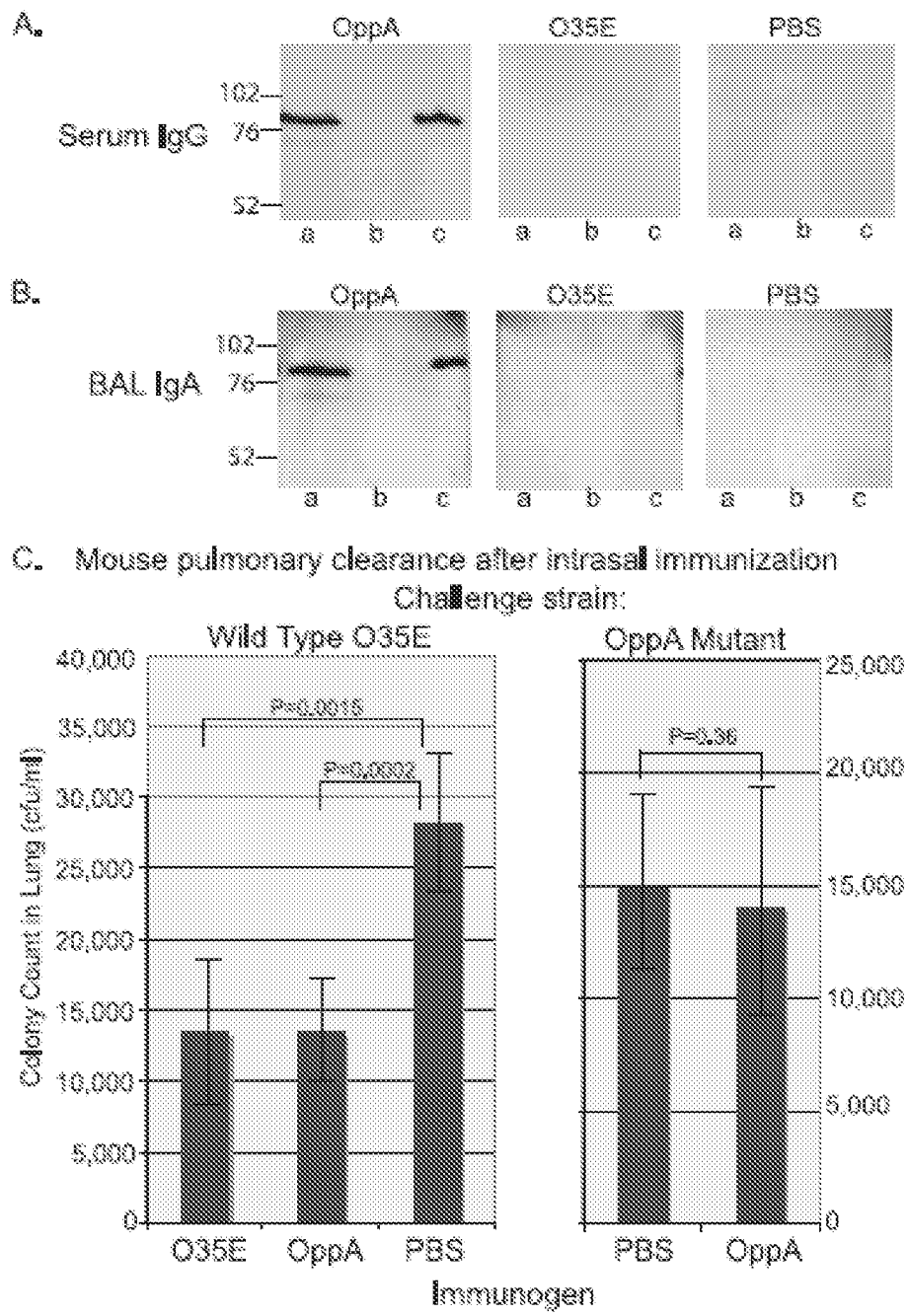
FIG. 7. Mucosal immunization of mice. Panel A. Immunoblot assays with sera (1:10,000) pooled from mice immunized intranasally with purified recombinant OppA (left panel), *M. catarrhalis* 035E (middle panel), and PBS (right panel). Blots were probed with peroxidase-conjugated anti-mouse IgG and developed with chemiluminescence. Panel B. Immunoblot assays with bronchoalveolar lavage (BAL) (1:50) pooled from mice immunized intranasally with purified recombinant OppA (left panel), *M. catarrhalis* 035E (middle panel), and PBS (right panel). Blots were probed with peroxidase-conjugated anti-mouse IgA and developed with chemiluminescence. For both A and B, lanes a, whole cell lysate of *M. catarrhalis* 035E; Lane b, whole cell lysate of OppA mutant; Lane c, recombinant OppA. Molecular mass markers are noted on the left in kilodaltons. C, Left panel. Results of pulmonary clearance after aerosol challenge with *M. catarrhalis* 035E following intranasal immunization of groups of mice with *M. catarrhalis* 035E, recombinant OppA, and PBS. C, right panel. Results of pulmonary clearance after aerosol challenge with OppA mutant following intranasal immunization of groups of mice with recombinant OppA and PBS as noted. For both panels in C: three hours post-challenge, bacteria present in mouse lung homogenate were plated and incubated overnight. Colony counts were plotted. Error bars represent the standard error of the mean (n=6). Statistical significance of difference between groups were analyzed by two-tailed t-test and p values are noted.

Mice immunized intranasally with OppA exhibited 1) production of anti-OppA antibodies in serum that recognized both native and recombinant OppA in immunoblot assays (FIG. 7A) 2) production of IgA antibodies to OppA in bronchoalveolar lavage fluid (FIG. 7B) and 3) significantly greater clearance of bacteria from lungs in the pulmonary clearance model (FIG. 7C, left panel). Intranasal immunization with OppA resulted in reduction of colony counts by approximately one half log as compared to the sham immunized control, an effect comparable to that induced by immunization with killed whole organisms (positive control). The experiment depicted in FIG. 7C was repeated and yielded an identical result of enhanced clearance by approximately one half log of bacteria. To further assess the specificity of the enhanced pulmonary clearance, groups of mice were immunized intranasally with OppA and with PBS (negative control) and were challenged with the OppA mutant. The level of clearance of the OppA mutant was no different in the OppA immunized group compared to the clearance observed in the PBS group (FIG. 7C, right panel). These results indicate that intranasal immunization with OppA induces enhanced clearance of *M. catarrhalis* in the mouse pulmonary clearance model. We conclude that mucosal immunization with purified recombinant OppA induces potentially protective immune responses against *M. catarrhalis*.

While specific embodiments have been presented in this description, those skilled in the art will recognize that routine modifications can be made by those skilled in the art without departing from the scope of the invention.

We claim:

1. A method of stimulating in an individual an immune response against *Moraxella catarrhalis* comprising administering to the individual a composition comprising isolated *Moraxella catarrhalis* OppA (Oligopeptide permease protein A) protein, wherein the isolated *Moraxella catarrhalis* OppA protein comprises the amino acid sequence of SEQ ID NO: 1, and wherein administering the composition results in a stimulated immune response against *Moraxella catarrhalis* in the individual.

2. The method of claim 1, wherein the composition further comprises an adjuvant.

3. The method of claim 2, wherein the adjuvant is a mucosal adjuvant.

4. The method of claim 1, wherein the composition further comprises a pharmaceutically acceptable carrier.

5. The method of claim 1, wherein the composition is administered to the individual by a route selected from subcutaneous, intramuscular, intravenous, intradermal, intranasal, oral and inhalation administrations.

6. The method of claim 1, wherein the stimulated immune response in the individual comprises generation of antibodies against *Moraxella catarrhalis*.

7. The method of claim 6, wherein the generation of antibodies comprises generation of IgG and/or IgA antibodies against *Moraxella catarrhalis*.

8. The method of claim 1, wherein the stimulated immune response is associated with an enhanced rate of *Moraxella catarrhalis* bacterial clearance from the lungs of an individual to whom the composition is administered.

9. The method of claim 1, wherein the composition is administered to the individual as several doses over a period of time.

10. The method of claim 1, wherein the stimulated immune response is prophylactic against *Moraxella catarrhalis* infection in the individual.

11. The method of claim 1, further comprising administering an antibiotic agent to the individual.

12. An immunogenic composition comprising isolated *Moraxella catarrhalis* OppA protein, wherein the isolated *Moraxella catarrhalis* OppA protein comprises the amino acid sequence of SEQ ID NO: 1, wherein administration of the immunogenic composition results in immune response against *Moraxella catarrhalis* in an individual.

13. The composition of claim 12, further comprising an adjuvant.

14. The composition of claim 13, wherein the adjuvant is a mucosal adjuvant.

* * * * *

UNITED STATES PATENT AND TRADEMARK OFFICE
CERTIFICATE OF CORRECTION

PATENT NO. : 8,501,197 B2
APPLICATION NO. : 13/695093
DATED : August 6, 2013
INVENTOR(S) : Murphy et al.

It is certified that error appears in the above-identified patent and that said Letters Patent is hereby corrected as shown below:

Title page, item (73), the Assignee should read:

--The Research Foundation for The
State University of New York, Amherst, New York (US)--

Signed and Sealed this
Twelfth Day of November, 2013

Teresa Stanek Rea
*Deputy Director of the United States Patent and Trademark Office*

SEQUENCE LISTING

```
<160> NUMBER OF SEQ ID NOS: 21

<210> SEQ ID NO 1
<211> LENGTH: 679
<212> TYPE: PRT
<213> ORGANISM: M. catarrhalis

<400> SEQUENCE: 1

Met Lys Lys Thr Lys Leu Phe Ala Thr Val Gly Ala Ala Val Leu Ser
1               5                   10                  15

Ala Ser Ile Leu Ala Ala Cys Ser Asn Asn Ser Thr Thr Ala Ser Gln
            20                  25                  30

Gly Gly Gly Asp Leu Thr Thr Tyr Lys Tyr Val Phe Ser Gly Asp Pro
        35                  40                  45

Lys Ser Leu Asp Tyr Ile Leu Ala Asn Gln Ala Val Thr Ala Asp Val
    50                  55                  60

Thr Thr Gln Met Val Asp Gly Leu Leu Glu Asn Asp Glu Tyr Gly Asn
65                  70                  75                  80

Leu Val Pro Ser Leu Ala Thr Asp Trp Ser Val Ser Glu Asp Gly Leu
                85                  90                  95

Thr Tyr Thr Tyr Thr Leu Arg Asp Gly Val Phe Trp Tyr Thr Ser Asp
                100                 105                 110

Gly Glu Glu Tyr Ala Pro Val Thr Ala His Asp Phe Val Thr Gly Leu
            115                 120                 125

Lys His Ala Val Asp Gly Lys Ser Asp Ala Leu Tyr Val Val Glu Asp
```

-continued

```
            130                 135                 140
Ser Val Lys Asn Leu Lys Ala Tyr Lys Glu Gly Lys Val Asn Trp Glu
145                 150                 155                 160

Glu Val Gly Val Lys Ala Leu Asp Asp Lys Thr Val Gln Tyr Thr Leu
                165                 170                 175

Asn Gln Pro Glu Ser Tyr Trp Asn Ser Lys Val Thr Tyr Ser Val Leu
            180                 185                 190

Phe Pro Val Asn Ala Lys Phe Leu Gln Ser Lys Gly Lys Asp Phe Gly
                195                 200                 205

Ala Leu Asp Pro Ser Ser Ile Leu Val Asn Gly Ala Tyr Phe Leu Ser
210                 215                 220

Ala Tyr Ala Ser Lys Ser Leu Met Glu Phe Thr Lys Asn Asp Asn Tyr
225                 230                 235                 240

Trp Asp Ala Asp Asn Val His Val Gln Ser Val Lys Leu Thr Tyr Thr
                245                 250                 255

Asp Gly Ser Asp Pro Gly Ser Tyr Tyr Arg Asn Phe Asp Lys Gly Glu
            260                 265                 270

Phe Ser Val Ala Arg Leu Tyr Pro Asn Asp Pro Thr Tyr Gln Ala Ala
                275                 280                 285

Ser Glu Lys Tyr Gln Asp Asn Ile Val Tyr Gly Leu Ile Asp Gly Thr
290                 295                 300

Thr Tyr Tyr Phe Thr Phe Asn Leu Asn Arg Ser Ala Phe Ala Asn Ser
305                 310                 315                 320

Thr Lys Thr Pro Glu Gln Gln Glu Ser Ala Lys Lys Ala Met Leu Asn
                325                 330                 335

Lys Asp Phe Arg Gln Ala Val Met Phe Ala Leu Asp Arg Ala Ala Tyr
            340                 345                 350

Gln Ala Gln Thr Val Gly Glu Ala Lys Thr Lys Ala Leu Arg Asn
            355                 360                 365

Met Leu Val Pro Pro Thr Phe Val Ser Ala Asp Gly Glu Asp Phe Gly
370                 375                 380

Gln Met Val Lys Lys Asp Leu Val Gly Tyr Gly Ala Glu Trp Gln Asp
385                 390                 395                 400

Val Asp Leu Ser Asp Ser Gln Asp Gly Leu Tyr Asn Pro Gln Lys Ala
                405                 410                 415

Lys Glu Glu Phe Ala Lys Ala Arg Gln Thr Leu Glu Ala Gln Gly Val
            420                 425                 430

Thr Phe Pro Ile Tyr Leu Asp Phe Pro Ile Asp Gln Ala Asp Ser Asn
            435                 440                 445

Arg Val Gln Gln Ala Gln Ser Phe Lys Gln Ser Val Glu Ala Ser Leu
450                 455                 460

Gly Gln Glu Asn Ile Ile Ile Asn Val Ile Glu Thr Glu Thr Ser Thr
465                 470                 475                 480

Tyr Glu Ser Gln Gly Tyr Ala Glu Ser Pro Glu Gln Gln Asp Tyr
                485                 490                 495

Asp Ile Met Met Ala Gly Trp Gly Pro Asp Tyr Gln Asp Pro Arg Thr
            500                 505                 510

Tyr Leu Asp Ile Met Ser Pro Ile Asp Gly Ala Met Leu Gln Lys Thr
            515                 520                 525

Gly Ile His Arg Gly Gly Asp Lys Ala Leu Val Lys Gln Val Gly Leu
            530                 535                 540

Asp Thr Tyr Gln Thr Leu Leu Asn Gln Ala Ser Val Ile Ser Asn Asp
545                 550                 555                 560
```

```
Asn Ser Ala Arg Tyr Asn Ala Tyr Ala Lys Ala Gln Ala Leu Leu Leu
                565                 570                 575

Asp Ser Ala Leu Gln Ile Pro Met Val Ala Ile Gly Val Pro Arg
            580                 585                 590

Val Ser Lys Gly Val Pro Phe Ser Gly Ser Phe Ser Trp Ala Gly Asn
            595                 600                 605

Lys Gly Gly Ser Trp Tyr Lys Arg Leu Lys Leu Gln Ala Gln Pro Ile
610                 615                 620

Thr Thr Glu Gln Tyr Glu Lys Ala Tyr Gln Ala Trp Gln Ser Glu Lys
625                 630                 635                 640

Ser Ala Ser Asn Ala Lys Tyr Ala Asp Ser Leu Val Asn Arg Val Lys
                645                 650                 655

Lys Ser Asp Thr Ala Ala Ser Asp Ala Ala Thr Asp Ala Ala Thr
            660                 665                 670

Thr Asp Thr Thr Thr Ala Asn
        675

<210> SEQ ID NO 2
<211> LENGTH: 2039
<212> TYPE: DNA
<213> ORGANISM: M. catarrhalis

<400> SEQUENCE: 2
atgaaaaaaa cgaagttatt tgccacagta ggggcagcag tattatcagc atctatttta      60
gctgcatgca gcaataatag cacgacagca tcacaaggtg gcggtgattt gaccacctat     120
aaatatgtgt tttcaggtga cccaaaatct ttagactata tcttagccaa ccaagctgtt     180
actgccgatg ttaccactca gatggttgat ggtttgctag aaaatgatga atatggcaac     240
cttgtccctt cttggcgac tgattggagc gtttcagaag atggattaac ttataccac      300 accttgcgtg atggggtatt tggtacact tcagatggcg aagaatatgc gcccgttact      360
gcccatgact ttgtgacagg tctaaaacat gccgttacg gtaaatctga tgcactttat      420
gtggttgaag attctgtaaa aaacctaaaa gcctataaag aaggtaaagt gaattgggaa     480
gaggttggcg ttaaggcttt agatgataaa actgtacaat acacgctaaa ccaaccagaa    540
tcatattgga attctaaagt gacctatagc gtcctattcc ctgtgaatgc taagttttta    600
caatctaaag gtaaagattt tggtgcttta gatccttcat ctattttggt caatggtgct    660 tacttttta gtgcctatgc atcaaaatct ttgatggaat ttactaaaaa tgataattat     720
tgggatgctg acaatgttca tgtacagtct gtcaagctaa cctataccga tggctcagat     780
cctggttcgt attatcgtaa cttttgataaa ggcgagttta gcgttgcacg cttatatcca     840
aatgacccaa cttaccaagc tgccagtgaa aaatatcaag ataacatcgt ttatggcttg     900
atagatggta caacttatta tttcaccttt aacctaaatc gttctgcttt tgccaatagc     960
acaaaaacgc agagcaaca gaatctgcc aaaaaggcaa tgctgaacaa agattttccgt    1020 caagcggtta tgtttgcact tgatcgtgca gcttatcaag cacaaactgt cggtgaggaa    1080
gccaaaacca aggccttgcg taatatgctg gtaccgccaa cttttgtgtc tgccgatggt    1140
gaagactttg ggcaaatggt gaaaaaagac ttggtaggct atggtgcaga tggcaagat      1200 gtcgatttgt cagatagcca agatggtcta caatccac aaaaagccaa agaagagttt    1260
gctaaagcca gacaaacttt agaagctcaa ggcgtgactt tccctatcta tttggatttt    1320
ccaattgacc aagcagattc gaacagagtt cagcaagctc aatcattcaa gcaatcggtt    1380
gaggcctcat tgggtcaaga aaatattatt atcaatgtca ttgaaaccga gacctcaact    1440
```

-continued

```
tatgagtctc aaggctacta tgctgaatcg ccagagcagc aagattatga tattatgatg   1500
gcaggttggg gcccggatta tcaagatcca cgcacctatt tggatatcat gagtcctatt   1560
gatggtgcca tgctacaaaa aacaggtatc cacagaggtg gcgataaagc tttagttaaa   1620
caagttggtt tggatactta tcaaacactg cttaatcagg catcggtcat ctctaatgat   1680
aacagtgcgc gttataatgc ctatgccaaa gcacaggcat tactgcttga cagtgcttta   1740
caaatcccaa tggttgctat tggtggtgta ccaagagttt ctaaaggcgt accatttagc   1800
ggatcatttt cttgggcggg caataaaggc ggtagctggt ataagagatt aaaactacaa   1860
gcacagccta tcacgactga gcaatatgag aaagcctatc aagcatggca agtgaaaaa    1920 tcggcttcta atgccaaata tgctgacagc cttgttaatc gtgtcaaaaa atcagataca   1980
gcagcaagcg atgctgcagc aactgatgct gcaaccacgg atacgacaac agcgaattg    2039
```

```
<210> SEQ ID NO 3
<211> LENGTH: 24
<212> TYPE: DNA
<213> ORGANISM: artificial sequence
<220> FEATURE:
<223> OTHER INFORMATION: olignonucleotide sequence primer

<400> SEQUENCE: 3
atgaaaaaaa cgaagttatt tgcc                                          24

<210> SEQ ID NO 4
<211> LENGTH: 21
<212> TYPE: DNA
<213> ORGANISM: artificial sequence
<220> FEATURE:
<223> OTHER INFORMATION: primer sequence

<400> SEQUENCE: 4
tcaattcgct gttgtcgtat c                                             21

<210> SEQ ID NO 5
<211> LENGTH: 20
<212> TYPE: DNA
<213> ORGANISM: artificial sequence
<220> FEATURE:
<223> OTHER INFORMATION: primer sequence

<400> SEQUENCE: 5
aatcaggcat cggtcatctc                                               20

<210> SEQ ID NO 6
<211> LENGTH: 20
<212> TYPE: DNA
<213> ORGANISM: artificial sequence
<220> FEATURE:
<223> OTHER INFORMATION: primer sequence

<400> SEQUENCE: 6
tcagtcgtga taggctgtgc                                               20

<210> SEQ ID NO 7
<211> LENGTH: 18
<212> TYPE: DNA
<213> ORGANISM: artificial sequence
<220> FEATURE:
<223> OTHER INFORMATION: primer sequence

<400> SEQUENCE: 7
gggatgctga caatgttc                                                 18
```

<210> SEQ ID NO 8
<211> LENGTH: 19
<212> TYPE: DNA
<213> ORGANISM: artificial sequence
<220> FEATURE:
<223> OTHER INFORMATION: primer sequence

<400> SEQUENCE: 8
tgtcattgaa accgagacc                                                  19

<210> SEQ ID NO 9
<211> LENGTH: 29
<212> TYPE: DNA
<213> ORGANISM: artificial sequence
<220> FEATURE:
<223> OTHER INFORMATION: primer sequence

<400> SEQUENCE: 9
atcgccatgg aagcaataat agcacgaca                                       29

<210> SEQ ID NO 10
<211> LENGTH: 28
<212> TYPE: DNA
<213> ORGANISM: artificial sequence
<220> FEATURE:
<223> OTHER INFORMATION: primer sequence

<400> SEQUENCE: 10
ggtcggatcc attcgctgtt gtcgtatc                                        28

<210> SEQ ID NO 11
<211> LENGTH: 22
<212> TYPE: DNA
<213> ORGANISM: artificial sequence
<220> FEATURE:
<223> OTHER INFORMATION: primer sequence

<400> SEQUENCE: 11
tctgacacgc tatcctcacg aa                                              22

<210> SEQ ID NO 12
<211> LENGTH: 34
<212> TYPE: DNA
<213> ORGANISM: artificial sequence
<220> FEATURE:
<223> OTHER INFORMATION: primer sequence

<400> SEQUENCE: 12
tagttagtca cttgtgatgc tgtcgtgcta ttat                                 34

<210> SEQ ID NO 13
<211> LENGTH: 34
<212> TYPE: DNA
<213> ORGANISM: artificial sequence
<220> FEATURE:
<223> OTHER INFORMATION: primer sequence

<400> SEQUENCE: 13
gcatcacaag tgactaacta ggaggaataa atgg                                 34

<210> SEQ ID NO 14
<211> LENGTH: 34
<212> TYPE: DNA
<213> ORGANISM: artificial sequence
<220> FEATURE:
<223> OTHER INFORMATION: primer sequence -continued

<400> SEQUENCE: 14
gccatgcttg cattattccc tccaggtact aaaa　　　　　　　　　　　　　　　34

<210> SEQ ID NO 15
<211> LENGTH: 34
<212> TYPE: DNA
<213> ORGANISM: artificial sequence
<220> FEATURE:
<223> OTHER INFORMATION: primer sequence

<400> SEQUENCE: 15
gggaataatg caagcatggc aaagtgaaaa atcg　　　　　　　　　　　　　　　34

<210> SEQ ID NO 16
<211> LENGTH: 20
<212> TYPE: DNA
<213> ORGANISM: artificial sequence
<220> FEATURE:
<223> OTHER INFORMATION: primer sequence

<400> SEQUENCE: 16
cacaagccct tctggtgatt　　　　　　　　　　　　　　　　　　　　　　　　20

<210> SEQ ID NO 17
<211> LENGTH: 20
<212> TYPE: DNA
<213> ORGANISM: artificial sequence
<220> FEATURE:
<223> OTHER INFORMATION: primer sequence

<400> SEQUENCE: 17
aagactttgg gcaaatggtg　　　　　　　　　　　　　　　　　　　　　　　　20

<210> SEQ ID NO 18
<211> LENGTH: 20
<212> TYPE: DNA
<213> ORGANISM: artificial sequence
<220> FEATURE:
<223> OTHER INFORMATION: primer sequence

<400> SEQUENCE: 18
tcagtcgtga taggctgtgc　　　　　　　　　　　　　　　　　　　　　　　　20

<210> SEQ ID NO 19
<211> LENGTH: 20
<212> TYPE: DNA
<213> ORGANISM: artificial sequence
<220> FEATURE:
<223> OTHER INFORMATION: primer sequence

<400> SEQUENCE: 19
aaggagaagt agcaaggagg　　　　　　　　　　　　　　　　　　　　　　　　20

<210> SEQ ID NO 20
<211> LENGTH: 19
<212> TYPE: DNA
<213> ORGANISM: artificial sequence
<220> FEATURE:
<223> OTHER INFORMATION: primer sequence

<400> SEQUENCE: 20
gaagatgaac aaagccctg　　　　　　　　　　　　　　　　　　　　　　　　　19

<210> SEQ ID NO 21
<211> LENGTH: 18
<212> TYPE: DNA

```
<213> ORGANISM: artificial sequence
<220> FEATURE:
<223> OTHER INFORMATION: primer sequence

<400> SEQUENCE: 21
acacttttac cgccttgg                                                    18
```